United States Patent [19]

Kirsch et al.

[11] Patent Number: 5,385,541
[45] Date of Patent: Jan. 31, 1995

[54] CEREBROSPINAL FLUID SHUNT CAPBLE OF MINIMAL INVASIVE REVISION

[75] Inventors: Wolff M. Kirsch, Redlands; Yong H. Zhu, Loma Linda, both of Calif.

[73] Assignee: Loma Linda University Medical Center, Loma Linda, Calif.

[21] Appl. No.: 874,293

[22] Filed: Apr. 24, 1992

[51] Int. Cl.⁶ .................................. A61F 2/20
[52] U.S. Cl. ............................ 604/8; 604/9; 604/34
[58] Field of Search ............ 604/8, 9, 10, 19, 27, 604/28, 30, 34, 35, 43, 48, 49, 93, 115, 167

[56] References Cited

U.S. PATENT DOCUMENTS

| | | | |
|---|---|---|---|
| 3,020,913 | 2/1962 | Heyer | 604/9 |
| 3,492,996 | 2/1970 | Fountain | 604/9 |
| 3,595,240 | 7/1971 | Mishler | |
| 3,654,932 | 4/1972 | Newkirk et al. | 604/9 |
| 3,894,541 | 7/1975 | El-Shafei | 604/99 X |
| 4,578,057 | 2/1986 | Sussman | |
| 4,583,967 | 4/1986 | Harris | 604/9 |
| 4,585,440 | 4/1986 | Tchervenkov et al. | |
| 4,601,724 | 7/1986 | Hooven et al. | 604/8 X |
| 4,767,400 | 8/1988 | Miller et al. | 604/8 |
| 5,030,210 | 7/1991 | Alchas | 604/9 X |
| 5,084,015 | 1/1992 | Moriuchi | 604/93 X |

FOREIGN PATENT DOCUMENTS

| | | |
|---|---|---|
| 0047013 | 3/1982 | European Pat. Off. |
| 0157906 | 10/1985 | European Pat. Off. |
| 0381062 | 8/1990 | European Pat. Off. |

Primary Examiner—Sam Rimell
Attorney, Agent, or Firm—Martens, Olson & Bear Knobbe

[57] ABSTRACT

A surgical shunt capable of revision and inspection on a minimal invasive basis is provided. The shunt comprises a ventricle tube and drain tube connected by an elbow. The elbow has branches and a bend therein so as to connect the tubes at nearly a right angle. A portal is mounted on the bend of said elbow. The portal comprises a concave slit valve and a portal cover thus forming a self-sealing access to the shunt. The portal is oriented on the elbow so as to allow passage therethrough into either of said tubes by an angioscope or other device. Thus, the angioscope or other device can be externally inserted into the interior regions of the shunt in order to remove blockages and improve cerebrospinal fluid flow without surgical procedures.

15 Claims, 4 Drawing Sheets

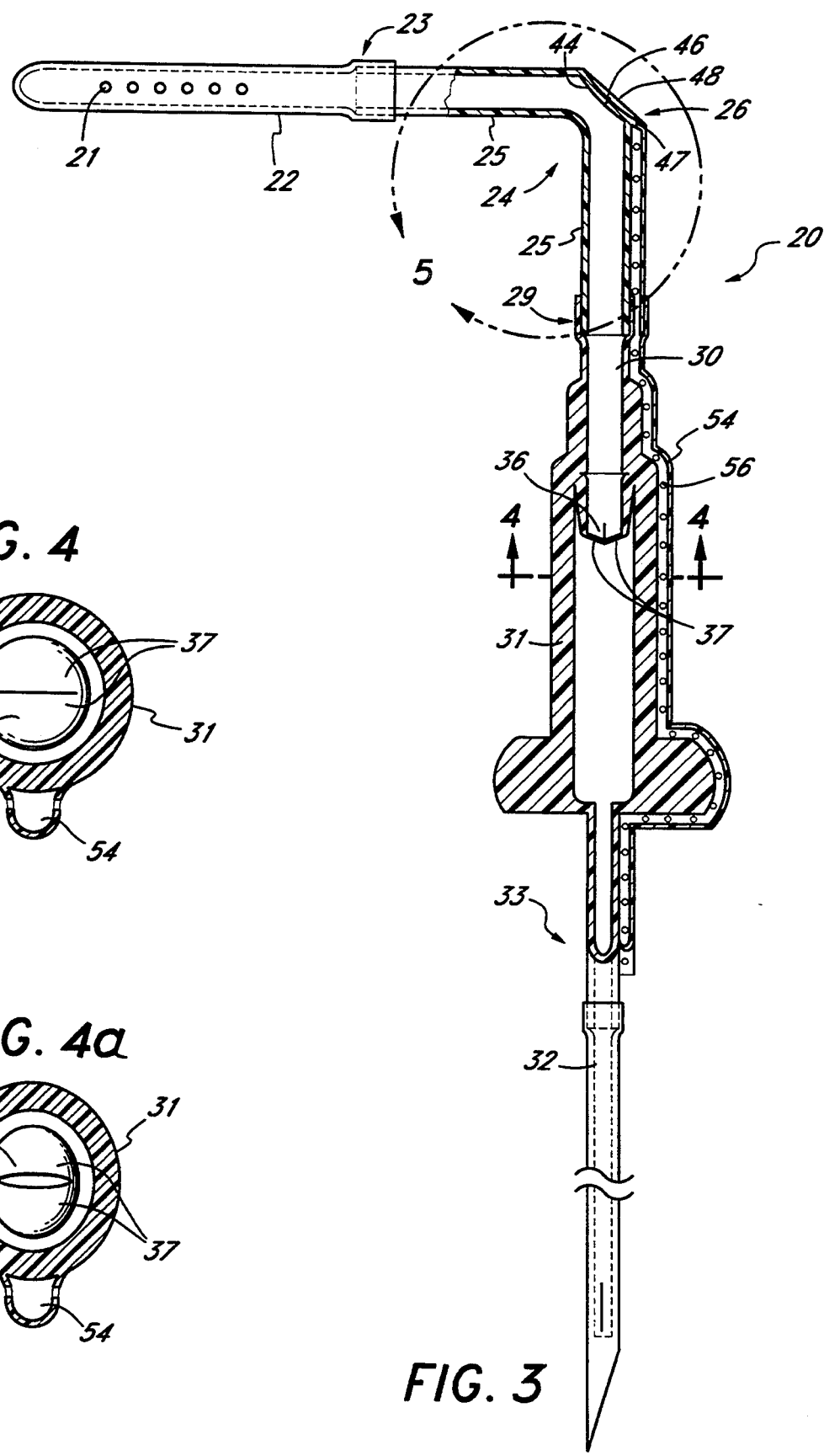

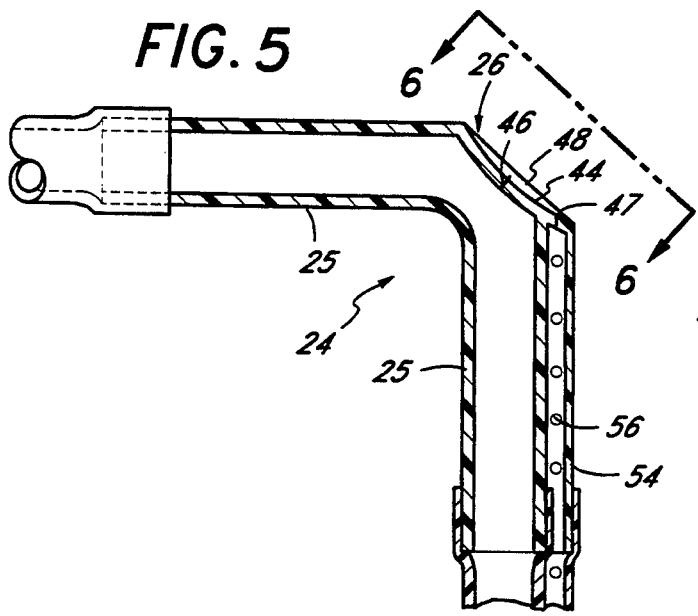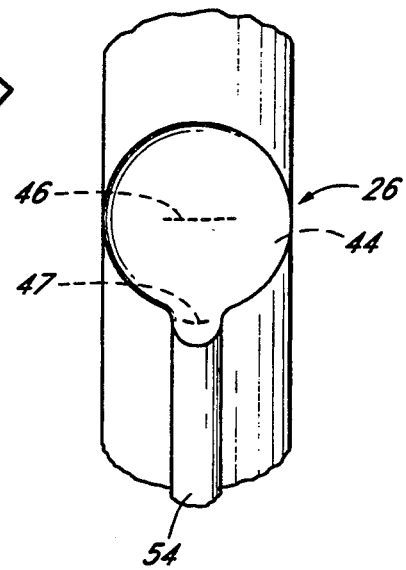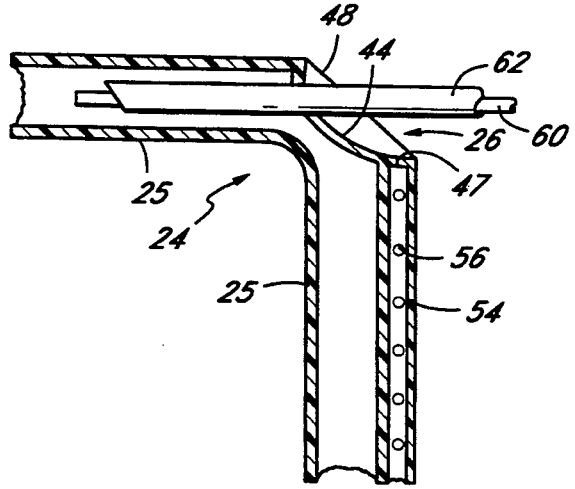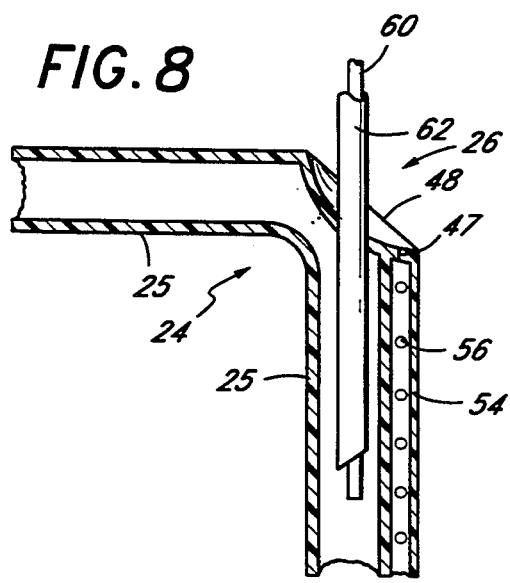

CEREBROSPINAL FLUID SHUNT CAPBLE OF MINIMAL INVASIVE REVISION

BACKGROUND OF THE INVENTION

The present invention relates to an improved cerebrospinal fluid ("CSF") shunt device, and, more particularly, to a CSF shunt which is capable of inspection and revision on a minimal invasive basis, thereby greatly reducing the pain and risk to the patient associated with previous shunt revision procedures. In addition, since the shunt revision can be performed on an out-patient basis, the cost of previous shunt revision surgical procedures is greatly reduced.

The valve regulated drainage of cerebrospinal fluid is an important neurosurgical intervention for the treatment of hydrocephalus, or "water on the brain." Hydrocephalus is caused by excess cerebrospinal fluid being located between the brain and skull. When congenital, hydrocephalus may result in excessive skull enlargement and, if untreated, progress to brain damage, or even death. When the condition occurs later in a person's life, the skull is no longer flexible and the condition can cause headaches, vomiting, and loss of coordination and mental functioning.

Hydrocephalus is commonly treated by providing a drain tube, known as a "shunt," between the source of the fluid within a ventricular cavity of the patient and another body cavity, such as the abdomen, chest, or vascular system (i.e., a major blood vessel, such as the jugular vein). Thus, in order to maintain the size of a child's skull at normal dimensions and to relieve pressure, the cerebrospinal fluid is drained or shunted to other parts of the body.

In order to install the shunt, a scalp incision is made and a small hole is drilled in the skull. The proximal end of the shunt is installed in the ventricular cavity. The distal end of the shunt is then installed in that portion of the body into which the cerebrospinal fluid is to be drained.

CSF shunts normally comprise a cannula or tubing system which is commonly fabricated from silastic, a material made by Dow-Corning. The ventricular or proximal end of the shunt is provided with small openings that vary from microns to millimeters in order to receive the cerebrospinal fluid into the shunt tubing. Likewise, the distal end of the shunt also is provided with small openings, often shaped as slits, to discharge the fluid from the shunt into the appointed body cavity. The shunts usually have an internal diameter of approximately 1.5 mm and are provided with a system of valves. The valves are generally one way, only allowing fluid to pass out of the ventricular cavity. Each valve is designed to open due to slight differential pressure between the inlet or proximal end of the shunt and its outlet or distal end. The valve will close in the event the pressure differential reverses, which may occur by coughing or straining of the patient, thereby preventing a reverse flow of blood or other fluid through the shunt into the ventricular cavity.

A typical CSF shunt is essentially L-shaped, except that it is installed in the skull of the patient in an inverted fashion. The shunt is comprised of various sections of tubing which are connected together. For example, the proximal or ventricular tube is inserted directly into the skull so as to be in communication with the ventricular cavity. This section of tubing is then connected, near the surface of the skull, to an elbow connector which forms a substantially 90° angle. The elbow connector is in turn typically connected to another section of tubing which leads to a pump tube situated just under the skin of the skull. Finally, an outlet or drain tube is connected to the pump tube which allows drainage of cerebral spinal fluid to another body cavity. Thus, the elbow connector is near the "corner" of the shunt in that it conducts fluid out of the skull and down the body tangentially to the skull. A portal is also installed at the corner, just below the skin, to provide access to the shunt by a hypodermic needle. This portal allows the physician to withdraw fluid from or give injections into the tissue surrounding the shunt. A shunt exhibiting this configuration, including the function of the pump tube, is described in U.S. Pat. No. 3,654,932 to Newkirk, et al.

Due to the relatively small openings at the ends of the shunt and at the valves, the major complications associated with CSF shunting are obstruction, infection and valve malfunction. Because of the minimal internal diameter of the shunt, obstructions caused by protein globules, choroid plexus and other small particulate are common. Further, because of the location of the shunt and the fact that the tissue surrounding the shunt area receives little circulation, infection in this area is common. These problems require at least shunt revision, and often complete replacement. More importantly, any of these problems is life threatening and previously required major neurosurgical intervention, including hospitalization, general anesthesia and incisions that spanned three body cavities (cranial, thoracic, abdominal). In addition, the frequency of shunt obstructions is quite high, varying from 10% to 30% in most series. Approximately 35,000 new CSF shunts are inserted each year and most remain in place for life, unless replacement is required. Therefore, the expense, discomfort, and risk to the patient associated with previous shunt revision surgical procedures are substantial.

Accordingly, there is a clear need for a CSF shunt device which can be revised on a minimal invasive basis.

SUMMARY OF THE INVENTION

The CSF shunt of the present invention satisfies the above-described need by providing a shunt device having an external access opening or external valve to permit endoscopic examination and procedural manipulation of infected or malfunctioning shunts. More specifically, the shunt of the present invention provides a valved access opening near the elbow connector of the shunt in order to permit insertion of a small angioscope or other device into the interior of the shunt. Because of the location and configuration of this access opening, the angioscope can be used to inspect both the distal and proximal regions of the shunt. In accordance with the improved shunt of the present invention, corrective procedures can be performed by means of the operating angioscope in order to clear the partially or completely occluded shunt or to correct valve malfunction, etc. In addition to these features, an external conduit delivery system is also provided for the shunt in which antibiotics or other therapeutic drugs can be delivered to the tissue surrounding the shunt site.

Accordingly, many substantial advantages are realized through the shunt of the present invention. First, inspection and revision of the shunt is possible on a minimal invasive basis, thus reducing the pain and risk associated with shunt revision procedures. Since revision can be performed on an out-patient basis, the expense of previous shunt revision surgery is greatly reduced. Moreover, because minimal invasive inspection is possible, shunts will be inspected more frequently in order to anticipate and avoid life threatening situations. The shunt of the present invention can also be ensured of exhibiting better performance and a longer life since revisions are more likely to occur. Moreover, because of improved shunt maintenance, replacement surgery will be required less often, again reducing danger and expense to the patient.

As explained briefly above, in a typical shunt installation, the pump tube is positioned just below the skin of the skull so as to be manually manipulated. Thus, the elbow connector of the shunt is likewise located near the surface of the skin. A valved portal is provided at the elbow of the shunt of the present invention and when the shunt is installed, the portal is situated parallel to the scalp. This portal is thus ideally situated on the bend of elbow to permit access into the shunt in both the proximal direction toward the ventricular end of the shunt, as well as downward along the pump and/or drain tubing and distal regions of the shunt.

The portal can take on various configurations which will permit insertion of a suitable trocar and angioscope, and is preferably in the nature of a concave slit valve, having a portal cover. An angioscope or other device can be inserted into the interior of the shunt and freely manipulated. On the other hand, when the angioscope or other device is removed, the portal is self-sealing, both preventing escape of cerebrospinal fluid and preventing entry into the shunt of outside substances. In this regard, the portal acts as a one-way valve. The material of the portal cover is a type of silicone. The concave valve is made of silastic.

The slit in the concave valve can be opened by direct manual pressure transmitted through the skin. Because the portal is located at the elbow of the shunt, the concave valve is only a few millimeters under the skin surface. The exact location of the shunt may be determined using X-rays. The surgeon may open the slit in the concave valve by pressing upon the scalp in an area proximal to the concave valve.

The portal is installed in tandem series to the shunt system and permits puncture through the skin by a suitable trocar. Once a trocar has been inserted into the shunt, a suitable cannula will serve as a guide for the angioscope. Preferably, such a trocar can take the form of an 18-gauge needle.

Thus, in accordance with a method of the present invention, the slit of the concave valve is first opened manually by direct pressure transmitted through the skin. An 18 gauge needle is then inserted through the scalp, portal cover, and the slit in the concave valve, and into the internal regions of the shunt. A cannula is inserted over the trocar and the trocar is removed. A 0.5 mm angioscope is then inserted through the cannula and into the shunt for visual inspection.

The angioscope permits easy visualization, for example, of the openings of the ventricular end of the shunt to determine whether or not it is blocked. Furthermore, the angioscope can be used to inspect the various tubing connections and valves to ensure proper drainage of fluid. If revision is necessary, various instruments can be inserted into the shunt through the channel of the angioscope. For example, the angioscope can be fitted with an excimer laser for the destruction of choroid plexus (the cerebrospinal fluid producing matter which often clogs the proximal end of the shunt) or other obstructive material. Alternately, an irrigation system for the infusion of fluids and antibiotics into the interior of the shunt, or a snipping device for removing other blockage, may be included on the angioscope. The angioscope can also be fitted with an anemometer to determine velocity and rate of CSF flow at any given point. In the event the laser is utilized to burn away obstructing tissue, the interior of the shunt system is provided with a reflective coating material so as to not absorb laser energy and prolong shunt life. Further, a nerve stimulating electrode may be used in conjunction with the angioscope.

In accordance with another feature of the present invention, the shunt is provided with an external conduit system for the delivery of antibiotics and other therapeutic substances to the tissues surrounding the shunt. The tissues surrounding the shunt installation location do not receive much circulation. Accordingly, delivery of antibiotics and other drugs intravenously is not generally effective. Accordingly, the external conduit of the present shunt, which runs parallel to the tubing of the shunt, can carry such therapeutic substances to the various regions surrounding the shunt and deposit them in the tissues through openings in the conduit. Again, access to the external conduit is provided through the external access opening of the portal area.

Accordingly, the shunt of the present invention provides a much needed improvement in shunt revision.

BRIEF DESCRIPTION OF THE DRAWINGS

FIG. 3 is a partial cross section of the shunt of the present invention illustrating the manner in which its various components are connected together and further illustrating the elbow region at the "corner" of the shunt containing the valve portal of the present invention;

FIGS. 4 and 4a are cross-sectional views of the present shunt taken along line 4—4 of FIG. 3 and illustrating the operation of the one-way internal valve of the shunt;

FIG. 5 is a cross-sectional view taken along line 5—5 and illustrating in more detail the elbow portion of the present shunt;

FIG. 6 is a top view taken along lines 6—6 of FIG. 5 and illustrating the valved portal of the present invention, including the opening to the therapeutic conduit thereof;

FIGS. 7 and 8 are cross-sectional views of the elbow of the present shunt, similar to FIG. 5, illustrating the method of use of the present shunt;

DETAILED DESCRIPTION OF THE INVENTION

Figure 1:
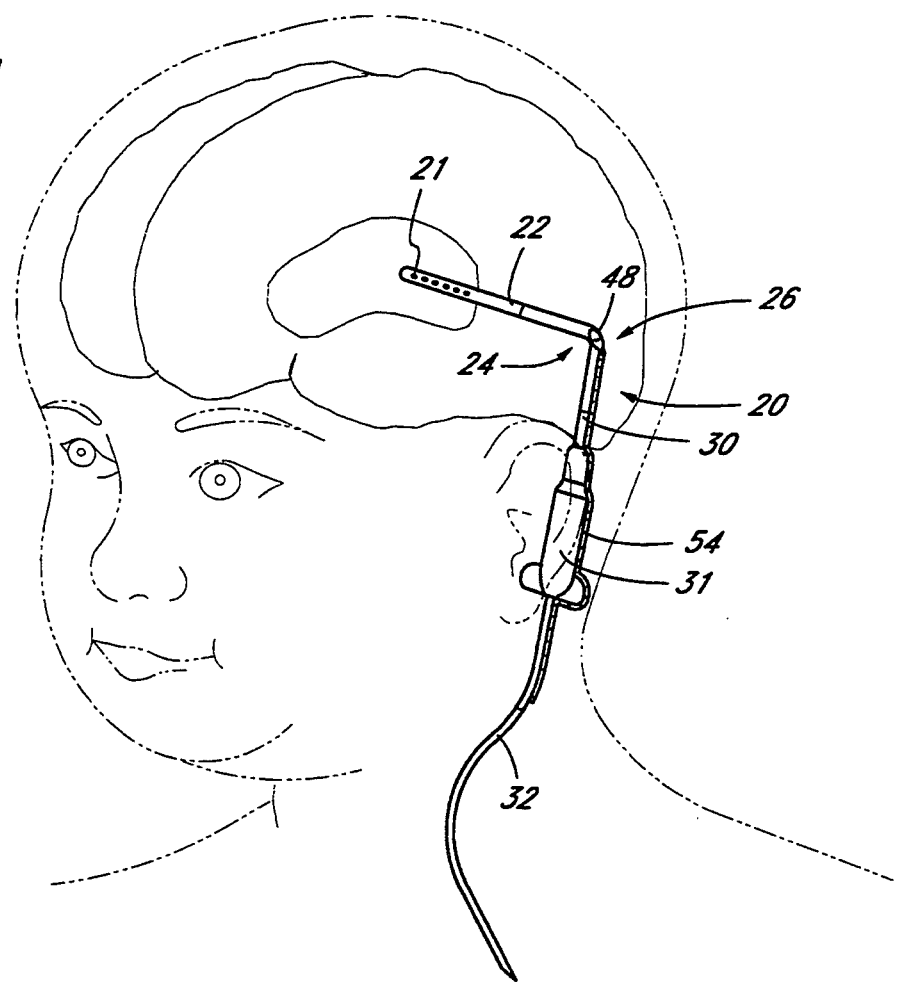
FIG. 1 illustrates in perspective view the location of the shunt of the present invention as installed in the skull of a patient.

Referring to FIG. 1, there is shown one embodiment of the CSF shunt 20 of the present invention as installed in the skull of a child. The shunt 20 comprises a ventricle tube 22, an elbow 24 located at the "corner" of the inverted L-shaped shunt 20, a portal region 26, a drain tube 30 and a long catheter 32 for draining the cerebrospinal fluid into a suitable body cavity. It should be noted that the ventricle tube 22 of the shunt 20 extends at an approximately 90° angle from the drain tube 30 portion thereof into one of the ventricles of the brain of the patient as illustrated best in FIG. 2. However, other specific configurations are achievable within the scope of the present invention, and the invention should not be construed to be limited to any particular shunt 20 location or placement. The placement illustrated in FIGS. 1 and 2 is exemplary only.

It will be noted that the ventricle tube 22 of the shunt 20 comprises a series of holes 21 or other openings to receive cerebrospinal fluid into the shunt 20 for purposes of draining to other body cavities. Draining is facilitated, in some embodiments, by means of a pump tube 31 which comprises a portion of the drain tube 30. Typically, the drain tube 30 is situated subcutaneously (e.g., just below the skin) and behind the ear of the patient. Thus, the physician is able to manipulate this pump tube 31 in order to modify the flow rate of cerebrospinal fluid and, in some instances, to clear obstacles. However, it should be pointed out that the present invention comprises substantial improvement over a pump tube 31 in terms of clearing obstacles or other impediments to cerebrospinal flow.

Thus, in operation, the shunt 20 of the present invention receives cerebrospinal fluid into the ventricle tube 22 and drains it, via the elbow 24, drain tube 30 and catheter 32, to other body cavities where it can be safely eliminated from the body in accordance with normal waste removal functions. However, an important advantage of the present invention is the facility of shunt 20 revision on a minimal invasive basis, clear drain obstacles and improve cerebrospinal flow, without major surgical intervention. These advantages are described below.

Figure 2:
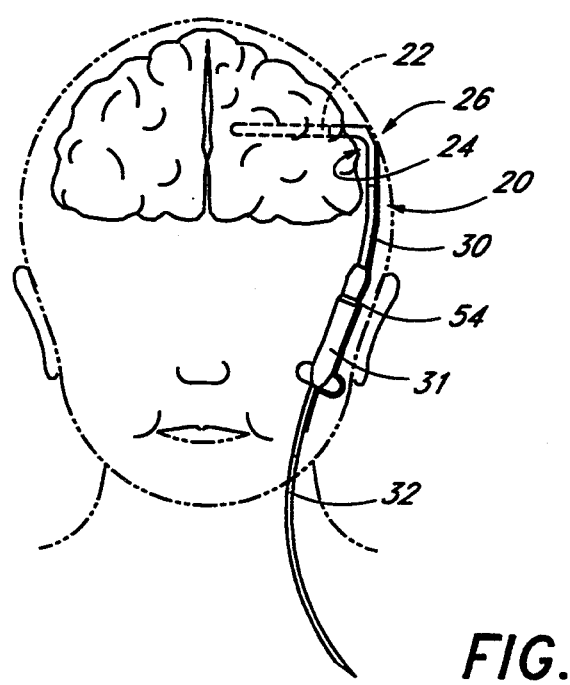
FIG. 2 is a front view similar to FIG. 1 illustrating the location and placement of the shunt of the present invention.

Referring first to FIG. 2, there is illustrated the placement of the elbow 24 of the shunt so as to be close to the surface of the skin, thereby providing access to the shunt 20 from external regions. Thus, the shunt 20 is illustrated in more detail in the partial cross-sectional view of FIG. 3.

Referring to FIG. 3, there is shown the ventricle tube 22 attached at its distal end 23 to the elbow 24, which is in turn attached to the proximal end 29 of the drain tube 30. Likewise, the distal end 33 of the drain tube 30 is attached to one end of the catheter 32. The elbow 24 of the present shunt 20 can be provided with connection systems at both of its branches which are well known by those of ordinary skill in the art. Preferably, the ventricle tube 22 and the drain tube 30 are connected to the branches 25 of the elbow 24 by means of a friction fit as shown in FIG. 3. However, other suitable connection mechanisms, such as connector devices, etc. are equally applicable. In addition, the corner of the elbow 24 is provided with a valve access portal 26 which is described below in more detail in connection with FIGS. 5-8.

The ventricle tube 22 has a internal diameter of approximately 1.5-2.0 millimeters, or other diameters sufficient to accommodate a 0.5 millimeter angioscope, as explained below in more detail. The length of the ventricle tube 22 is determined by the age of the patient.

The other branch 25 of the elbow 24 is connected to a drain tube 30 which includes a pump tube 31, mentioned above, and an external conduit 54 for providing therapeutic medications to the tissue surrounding the shunt 20. Typically, the drain tube 31 also includes a one-way valve 36, as shown in FIG. 3, which prevents the backflow of cerebrospinal fluid, as described below in more detail in connection with FIGS. 4 and 4a. However, it should be pointed out that many configurations and structures relating to the drain tube 30 are within the principles of the present invention.

The therapeutic conduit 54 comprises an external lumen which runs parallel along the length of the drain tube 30. Preferably, the therapeutic conduit 54 is virtually coextensive with the drain tube 30; however, other configurations are possible, and it is even within the scope of the present invention that the therapeutic conduit 54 extend along the length of the catheter 32. As noted in FIG. 3, the therapeutic conduit 54 contains a number of openings 56 along its length such that antibiotics or other medications injected into the conduit 54 through the portal 26 (in a manner described below in more detail in connection with FIG. 6) will be carried along the length of the shunt 20, and drained externally into the surrounding tissues for therapeutic purposes.

FIGS. 4 and 4a illustrate the function of the one-way valve 36 of the present shunt, sometimes referred to as a duck bill type valve. This valve 36 is located distally with respect to the drain end 30 of the elbow 24 and allows fluid to naturally pass only in one direction; that is, from the elbow 24 through the drain tube 30 and into the catheter 32. The valve 36 is constructed such that it opens automatically when the pressure differential between the elbow 24 and the catheter 32 becomes great enough. The valve 36 may be opened manually as well by transmission of pressure through the skin. That is, the valve 36 is molded as part of the drain tube 30 so that when the drain tube is pressed manually, the valve 36 will automatically open as shown in FIG. 4a. When fluid pressure or manual pressure is relieved, the flaps 37 of the valve 36 elastically return to their normally closed position, as illustrated in FIGS. 3 and 4. Although such valves 36 are common in the previous shunts, it will be noted that the methodology of the present invention includes the passage of angioscopes and other instruments through this one-way valve 36 for distal inspection and corrective procedures. Thus, it is preferred that any such valves 36 provide a valve open diameter of at least 0.5 millimeter or more.

A catheter 32 portion of the shunt 20 is located at the distal end 33 of the drain tube 30 and extends under the skin to a site to which the fluid is shunted. The catheter 32, as well known in the art, is a section of tubing which also may include one or more one-way valves (not shown). Again, preferably, the internal diameter of the catheter 32 should be at least 0.5 millimeters or greater in order to accommodate a suitable angioscope.

FIG. 5 is a close-up cross-sectional view of the elbow 24 portion of FIG. 3. As shown in FIG. 5, suitable friction fit connections can be made at both branches 25 of the elbow 24 in order to attach the ventricle 22 and drain tubes 30 thereto. It will be noted that, in connection with the drain tube 30, a double lumen connector is necessary in order to accommodate the therapeutic conduit 54 described above.

FIGS. 5 and 6 illustrate the portal 26 region off the elbow 24, including the dual-slit 46, 47 access openings, one for the main shunt 20 access and one for the therapeutic conduit 54 access. These valve openings 46, 47 are shown in more detail in FIG. 6, which is a front view of the portal 26 as taken along lines 6—6 of FIG. 5. As shown in FIGS. 5 and 6, the portal 26 is mounted at the bend in the elbow 24. The portal 26 comprises a concave valve 44 having first and second slits 46, 47 located therein, and a portal cover 48. The portal 26 is preferably mounted to the bend of the elbow 24 such that a trocar or other device may be inserted through it and directly into either branch of the elbow in a straight line. Normally, therefore, the portal 26 is mounted perpendicular to an imaginary line which bisects the center line of the branch of the elbow 24.

The concave valve 44 is, as best illustrated in FIG. 6, a slit valve formed from a concave disc. The slit 46 of the concave valve 44 is preferably oriented horizontally, as shown, but may also be oriented vertically in order to provide improved lateral access and movement for an angioscope 64, as described below in more detail. In fact, in some embodiments, it is preferable that the valve 44 be a four-quartered or four-flapped valve in order to enhance access and manipulation of the angioscope. The concave valve 44 may be formed directly as part of the elbow 24, or it may be formed separately and then securely affixed to the elbow 24 with adhesive. While it is preferred that the valve be concave, it is possible for the valve to be flat or even convex.

The concave valve 44 is preferably made from silastic so that it is sturdy, yet somewhat flexible. The first slit 46 is placed in the middle of the valve 44 to allow access through the valve 44 to the inside of the elbow 24. The slit 46 is sufficiently long to accommodate such items as trocars, angioscopes and the like. The flexibility of the valve 44 allows it to accommodate the manipulation of the angioscope 64 as it performs its inspection and cleaning function in both the ventricle 22 and drain tube 30. A second slit 47 is located below the first slit 46 and provides access to the conduit 54.

The portal cover 48 is a membrane covering the concave valve 44. The portal cover 48 is a self-sealing seal preferably made from silicone or other biocompatible material so that it is very elastic. The portal cover 48 is stretched across the open side of the concave valve 44. The cover 48 may be attached to the concave valve 44 by gluing or other attachment means well known in the art. The portal cover 48 is preferably attached so that when a trocar or cannula is removed from it, the cover 48 returns to its original closed state.

It is not absolutely necessary for the portal to have a cover 48. However, the risk of leakage through the portal 26 from the shunt 20 is greatly increased if a cover is not provided. It is also possible that only a portal cover 48 and no concave valve 44 be used.

The conduit 54 is accessed through the portal 26, as noted above. The inside of the conduit 54 may be accessed by piercing the portal cover 48 and opening the second slit valve 47. The conduit 54 allows the passage of fluid, such as antibiotics, through it and out the drain holes 56 into the surrounding tissue. Access and injection into the conduit may be accomplished by a hypodermic needle.

The method of the present invention, including the means of use of the portal 26 thereof may be described in connection with FIGS. 7-8. The shunt 20 is installed in the fashion well known in the art. However, careful attention is given, however, to the elbow 24 and portal 26 to ensure that the portal 26 is placed near the surface of the skin and oriented so that the skin and portal cover 48 are substantially parallel. Once in place, this shunt 20, like others, is located completely under the skin so as not to be visible or otherwise accessible without penetration of the skin.

Access to the inside of the shunt 20 is accomplished by, first, inserting a trocar 60, such as a 18-gauge needle, first through the skin covering the portal 26. The portal 26 may be located through use of an X-ray and digital pressure. Once located, the slit valve 46 is pressed open by pressing the concave valve 44 with fingers. The pressure is provided on the outside of the scalp, and transmitted to the slit 46. Pressure on the concave valve 44 aids in opening the silt 46 so that the trocar 60 may be passed therethrough. Once the slit 46 is slightly opened, the trocar 60 may be pushed through the elastic portal cover 48, through the slit 46 and into the inside of the elbow 24. Once the trocar 60 is placed, a cannula 62 may be slipped over it and guided into the shunt 20.

The direction at which the trocar 60 penetrates the portal 26 is important. Since the portal 26 is mounted on the bend or corner of the elbow 24, either branch of the elbow 24 may be accessed, depending on the entry angle of the trocar 60. As can be seen in FIGS. 7 and 8, the trocar 60 should pierce the portal 26 so that the trocar is parallel to the branch 25 in which it is to be inserted. It will be noted that the portal 26 design of the present invention, trocar 60 and angioscopic 64 access are available to either branch of the elbow without removing the trocar or angioscope. Therefore, the physician is able to inspect and perform corrective procedures in either the ventricle 22 or the drain 30 tube, including the catheter 32. This is an important advantage of the present invention which greatly facilitates shunt 20 revision. Furthermore, it is possible to provide an elbow of various configurations in order to accommodate trocar and angioscope manipulations. For example, the elbow 22 cross section, at the corner, can be made wider in order to permit trocar/angioscopic manipulation without contact to the internal surfaces of the shunt 20, thereby avoiding damage thereto and prolonging shunt life. Thus, the portal 26 may be constructed with a flat valve or even convex valve in order to increase the manipulation space inside the elbow 24.

Furthermore, it will be noted that the portal 26 is situated to the outside portion of the elbow 24 near the skin. Therefore, the cerebrospinal fluid is not likely to leak out of the valve 44 opening of the elbow 24 since the force of gravity will cause it to immediately drain downwardly upon reaching the corner of the elbow 24. However, even if fluid does reach the slit valve 44 of the portal 26, the slit construction and the flaps of the valve 44 will prevent leakage. Leakage can fully be prevented by a portal cover 48, as explained above.

Figure 9:
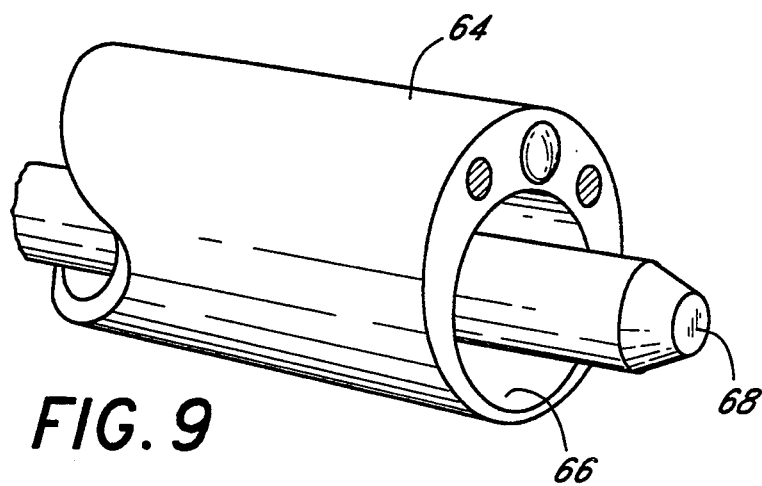
FIGS. 9-11 are perspective views of an angioscope device illustrating various instruments which can be utilized in connection therewith for minimal invasive shunt revision and inspection.
Figure 10:
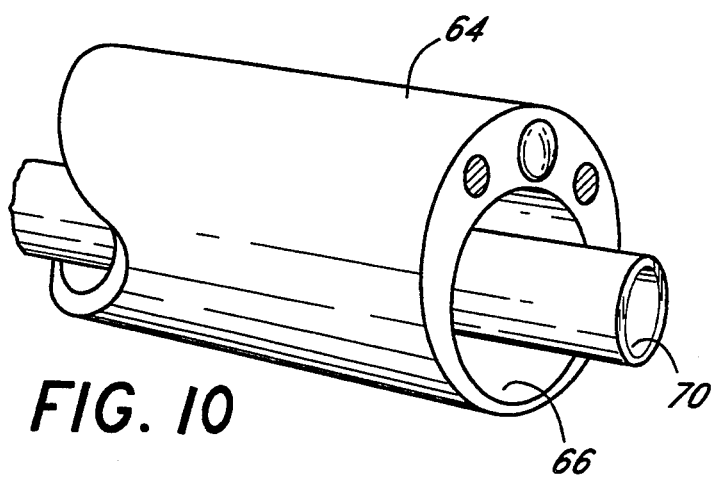
Figure 11:
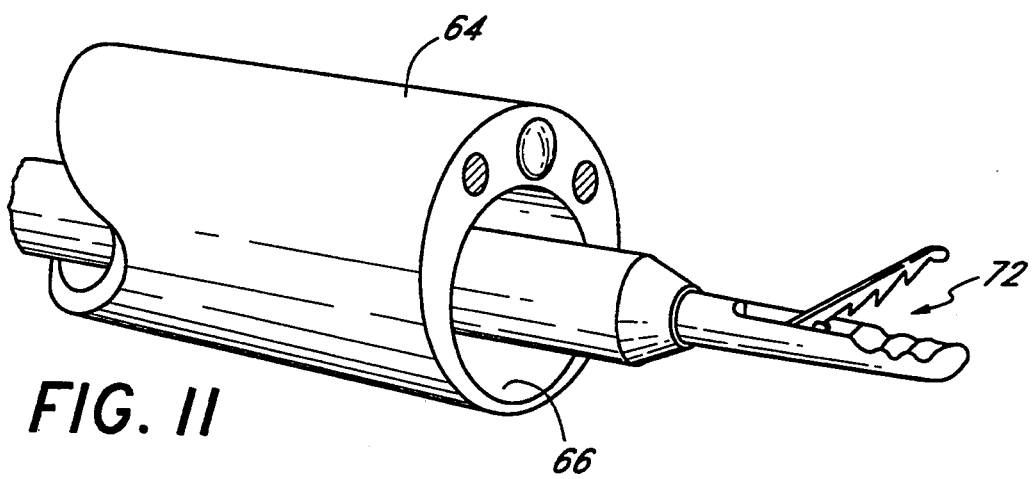

The various corrective procedures that can be accomplished with the present invention are illustrated in connection with FIGS. 9-11.

Once the cannula 62 is placed over the trocar 60 and inserted slightly into the desired arm of the elbow 26, a variety of devices may be inserted through the cannula. For example, a 0.5 mm angioscope 64 may be used, depending on the exact inner dimensions of the shunt 20. A 0.5 mm angioscope 64 is preferred since it requires a small cannula 62 for insertion, may easily be passed through the valves 36 in the shunt 20, and may easily be maneuvered. The angioscope 64 may be used to view the inside of the shunt to check for valve malfunction, separation of any of the various component parts of the shunt, or blockage in any area of the shunt. One such angioscope 64, having an internal lumen 66, is shown in FIG. 9. Angioscopes 64 of this type are fairly common in the prior art and within the knowledge of a person of ordinary skill.

Furthermore, the angioscope 64 can be used in combination with other instruments which are inserted into the shunt 20 through the lumen 66 of the angioscope. For example, as shown in FIG. 9, an excimer laser 68 can be inserted through the angioscope 64 and used to destroy choroid plexus, which often grows into the proximal end of the ventricle tube.

Furthermore, a hot-film anemometer (not shown) may be extended from the angioscope 64 into the shunt 20 at various locations in order to measure the flow rate of the cerebrospinal fluid. As illustrated in FIG. 10, an irrigation system 70 fitted to the angioscope 64 is particularly useful in introducing various fluids and antibiotics into the shunt 20. This is particularly useful since many infections manifest themselves inside the shunt 20 itself. In addition, a snipping device 72, as shown in FIG. 11, can also be utilized in connection with the angioscope 64 to remove blockages.

In this manner, the operating condition of the shunt 20 may easily be examined and evaluated, without the need to remove or expose the shunt. Further, blockages and other problems may easily be remedied without the time and cost associated with replacing a non-functioning shunt.

For infections occurring outside the shunt 20, such as in areas surrounding the shunt insertion site, use of the conduit 54 to place antibiotics is particularly useful. The conduit 54 is separately accessed through the portal 26. It is preferred that any cannula 62 or trocar 60 inserted into the shunt 20 be removed from the portal 26 before the conduit 54 is accessed. If more than one cannula 62 or trocar 60 is inserted into the portal, the portal cover 48 may tear, causing the seal to be broken.

The conduit 54 is accessed by inserting a trocar 60, preferably appropriately sized needle, into the scalp. Pressure is exerted on the scalp surrounding the trocar to open the second slit 47 in the concave valve 44. Once open, the trocar 60 may be pressed into the conduit 54 through the portal cover 48 and the second slit 47. Once in place, antibiotics may be introduced into the conduit 54. The antibiotic will travel down the conduit 54, exiting into the tissue surrounding the shunt 20 through the drain holes 56.

Advantageously, once any cannula 62 or trocar 60 is removed from the portal 26, the portal seals itself securely, preventing the release of fluid from the shunt 20 into the surrounding tissue, or vice versa. This is because when the trocar 60 or cannula 62 is removed, the slits 46, 47 automatically close, and the portal cover 48 elastically rebounds to a sealed state.

The shunt 20 of the present invention can be constructed from any suitable biocompatible material well known to those of ordinary skill in the art. In addition, it is preferable that the inside surfaces of the shunt 20 be lined with a material which is smooth and reflective. In this fashion, friction between the various instruments inserted into the shunt will be reduced. Furthermore, the light emanating from the angioscope 64 will be reflected in order to improve the vision in the deeper regions of the shunt 20. The interior of the shunt 20 system can be treated with a suitable coating so that laser energy is not absorbed, thereby prolonging the life of the shunt.

It will be understood that the above-described arrangements of apparatus and the methods therefrom are merely illustrative of application of the principles of this invention, and many other embodiments and modifications may be made without departing from the spirit and scope of the invention.

What is claimed is:

1. A shunting device for cerebrospinal fluid adapted to be implanted in part in the skull of a patient, said device having interior and exterior surfaces and comprising:

a ventricle tube adapted t be inserted through the skull and into the ventricle of the patient, said ventricle tube having openings for receiving said fluid into said ventricle tube for draining said fluid to another location;

a drain tube in fluid communication with said ventricle tube for draining said fluid to another location within the patient, said drain tube having openings too allow said fluid to drain out of said shunting device, said ventricle tube and said drain tube being joined at a junction;

a surface formed at said junction and angularly disposed with respect to both said ventricle tube and said drain tube; and an opening formed in said surface to externally receive an endoscopic device for inspecting and cleaning said shunting device, said opening being located on said shunting device such that said endoscopic device can access substantially the entire length of both said ventricle tube and said drain tube;

wherein the interior surfaces of said shunting device are coated with a material which is non-light absorptive, whereby laser light will not damage said shunting device.

2. A shunting device for cerebrospinal fluid adapted to be implanted in a patient, comprising:

a ventricle tube inserted into the ventricle of the patient;

a drain tube for draining said fluid to another location within the patient, said ventricle tube and said drain tube in fluid communication at a junction and forming an angle with one another at said junction;

an access portal formed in said shunting device at said junction;

a first opening in said portal and in fluid communication with said shunting device for receiving an endoscopic device into said shunting device for inspection and cleaning;

an external conduit formed along at least one portion of said shunting device and extending substantially parallel thereto; and a second opening formed in said portal and in fluid communication with said external conduit for introducing into said external conduit therapeutical medications and the like, said external conduit having openings to allow the escape of said therapeutic medications and the like into the tissues surrounding said shunting device in order to combat infection.

3. The shunting device of claim 2, wherein said first and second openings comprise slit valves which are substantially self-sealable.

4. A method for inspecting and cleaning cerebrospinal fluid shunting devices implanted in the body of a patient, comprising the steps of:

(a) inserting an endoscope into the shunt;

(b) inspecting both proximal and distal regions of said shunt without removing the endoscope therefrom;

(c) inspecting the interior regions of said shunt for occlusions or defects; and (d) inserting through a channel formed in the endoscope an endoscopic instrument for revising said shunt in accordance with the results of the inspection step.

5. The method of claim 4, wherein said insertion step (a) further comprises:

(a) inserting a trocar into said shunt;

(b) inserting the endoscope through said trocar and into said shunt; and (c) removing said trocar.

6. The method of claim 4, wherein said insertion step (c) further comprises inserting a laser through said endoscope and into said shunt for destroying occluding material, whereby the shunt may be cleaned.

7. A shunting device for cerebral spinal fluid adapted to be implanted in part in the skull of a patient, comprising:

a ventricle tube adapted to be inserted through the skull and into the ventricle of the patient, said ventricle tube having openings for receiving said fluid into said ventricle tube for draining said fluid to another location;

a drain tube in fluid communication with said ventricle tube for draining said fluid to another location within the patient, said drain tube having openings to allow said fluid to drain out of said shunting device; and an opening formed in said shunting device and adapted to externally receive an endoscopic device for inspecting and cleaning said shunting device, said opening located on said shunting device such that said endoscopic device can access both said ventricle tube and said drain tube, said shunting device forming an elbow and said opening being located substantially at said elbow, said opening comprising an access valve angularly formed in said elbow so as to provide access for said endoscopic device to both said ventricle tube and said drain tube, said valve comprising a concave structure formed from an elastic material, whereby manipulation of said endoscopic device wherein said shunting device is facilitated.

8. A shunting device for cerebral spinal fluid adapted to be implanted in part in the skull of a patient, comprising:

a ventricle tube adapted to be inserted through the skull and into the ventricle of the patient, said ventricle tube having openings for receiving said fluid into said ventricle tube for draining said fluid to another location;

a drain tube in fluid communication with said ventricle tube for draining said fluid to another location within the patient, said drain tube having openings to allow said fluid to drain out of said shunting device; and an opening formed in said shunting device and adapted to externally receive an endoscopic device for inspecting and cleaning said shunting device, said opening being located on said shunting device such that said endoscopic device can access both said ventricle tube and said drain tube, the interior surfaces of said shunting device being coated with a material which is non-light absorptive, whereby laser light will not damage said shunting device.

9. A method for inspecting and cleaning cerebral spinal fluid shunting devices implanted in the body of a patient, comprising the steps of:

(a) inserting a trocar into said shunt;

(b) inserting an endoscope through said trocar and into said shunt;

(c) removing said trocar;

(d) inspecting the interior regions of said shunt for occlusions or defects; and (e) inserting through a channel formed in the endoscope an instrument for revising said shunt in accordance with the results of the inspection step.

10. An elbow connector for a cerebral spinal fluid shunting device having a ventricle tube and a drain tube, the connector comprising:

a ventricle tube portion adapted to be connected to the ventricle tube of said shunting device;

a drain tube portion adapted to be connected to the drain tube of said shunting device;

a connector portion connecting said ventricle tube portion and said drain tube portion, whereby said ventricle tube and said drain tube of said shunting device are in fluid communication with one another, said connector portion forming an obtuse angle with respect to the axes of both said ventricle tube portion and said drain tube portion; and an opening formed in said connector portion for providing external access to both said ventricle tube and said drain tube of said shunting device.

11. The elbow connector of claim 10, wherein said ventricle tube portion comprises a dual conduit, including a first conduit for draining cerebral spinal fluid and a second conduit for receiving and distributing therapeutic substances.

12. The elbow connector of claim 10, wherein said opening comprises a slit valve.

13. The elbow connector of claim 10, wherein said opening comprises a concave valve.

14. The elbow connector of claim 10, wherein said opening is provided with a membrane cover.

15. The elbow connector of claim 10, wherein said drain tube portion comprises a dual conduit, including a first conduit for draining cerebral spinal fluid and a second conduit for receiving and distributing therapeutic substances.

* * * * *